United States Patent
Johansson

(10) Patent No.: US 10,220,196 B2
(45) Date of Patent: Mar. 5, 2019

(54) TATTOO MACHINE POWER SUPPLY

(71) Applicant: Ink Machines Sweden AB, Växjö (SE)

(72) Inventor: Christian Johansson, Växjö (SE)

(73) Assignee: Ink Machines Sweden AB (SE)

(*) Notice: Subject to any disclaimer, the term of this patent is extended or adjusted under 35 U.S.C. 154(b) by 360 days.

(21) Appl. No.: 15/104,891

(22) PCT Filed: Dec. 18, 2013

(86) PCT No.: PCT/SE2013/051553
§ 371 (c)(1),
(2) Date: Jun. 15, 2016

(87) PCT Pub. No.: WO2015/094042
PCT Pub. Date: Jun. 25, 2015

(65) Prior Publication Data
US 2017/0021154 A1    Jan. 26, 2017

(51) Int. Cl.
*A61M 37/00* (2006.01)

(52) U.S. Cl.
CPC . *A61M 37/0076* (2013.01); *A61M 2205/3561* (2013.01); *A61M 2205/502* (2013.01); *A61M 2205/8206* (2013.01); *A61M 2205/8237* (2013.01); *A61M 2209/01* (2013.01); *A61M 2210/04* (2013.01)

(58) Field of Classification Search
CPC .................................................. A61M 37/0076
See application file for complete search history.

(56) References Cited

U.S. PATENT DOCUMENTS

| | | | |
|---|---|---|---|
| 6,550,356 | B1 | 4/2003 | Underwood |
| 7,969,715 | B2 | 6/2011 | Copeland et al. |
| 2006/0064310 | A1 | 3/2006 | Briggs et al. |
| 2008/0033356 | A1 | 2/2008 | Kluge et al. |
| 2008/0033470 | A1 | 2/2008 | Kluge et al. |
| 2008/0077170 | A1 | 3/2008 | Kluge et al. |
| 2009/0125049 | A1 | 5/2009 | Copeland et al. |
| 2010/0241151 | A1 | 9/2010 | Rickard |
| 2011/0288575 | A1 | 11/2011 | Colton et al. |
| 2012/0265143 | A1 | 10/2012 | Krumme et al. |
| 2013/0096599 | A1 | 4/2013 | Colton et al. |
| 2015/0164543 | A1 | 6/2015 | Kluge |
| 2016/0164519 | A1* | 6/2016 | Arriaga ............. A61M 37/0076 606/186 |

* cited by examiner

*Primary Examiner* — Fritz M Fleming
(74) *Attorney, Agent, or Firm* — Condo Roccia Koptiw LLP

(57) ABSTRACT

A method of controlling a tattoo machine power supply (14), comprises detecting a user interaction with the tattoo machine power supply (14); based on said user interaction, generating an activation signal; wirelessly transmitting the activation signal; and setting the tattoo machine power supply (14) in an active state, in which it is responsive to remote control commands.

12 Claims, 3 Drawing Sheets

TATTOO MACHINE POWER SUPPLY

CROSS REFERENCE TO RELATED APPLICATIONS

This application is the National Stage Entry under 35 U.S.C. § 371 of Patent Cooperation Treaty (PCT) Application No. PCT/SE2013/051553, filed Dec. 18, 2013, the contents of which are hereby incorporated by reference in their entirety.

FIELD OF THE INVENTION

The present invention relates to a tattoo machine power supply and a method of controlling a tattoo machine power supply. It also relates to a tattoo machine controller unit and a method of operating a tattoo machine controller unit.

BACKGROUND OF THE INVENTION

Typically, a tattoo system comprises a controller unit, one or several hand-held tattoo machines connected to the controller unit, and a foot pedal connected to the controller unit for starting and stopping the tattoo machine(s). The controller unit typically has a user interface for setting and displaying the drive voltage supplied to the tattoo machine(s). In order to protect their clients as well as themselves from biological contamination, tattoo artists typically wear disposable gloves and protect their equipment using disposable plastic covers when creating body artwork. U.S. Pat. No. 7,969,715 provides an overview of currently employed methods of maintaining tattooing equipment clean and sterile. As hygiene is of vital importance, there is a constant strive in the tattooing business to even further improve sterility and cleanliness of the tattooing process.

SUMMARY OF THE INVENTION

It is an object of the present invention to solve, or at least mitigate, parts or all of the above mentioned problems. To this end, there is provided a method of controlling a tattoo machine power supply, the method comprising detecting a user interaction with the tattoo machine power supply; based on said user interaction, generating an activation signal; wirelessly transmitting the activation signal; and setting the tattoo machine power supply in an active state, in which it is responsive to remote control commands. Thereby, a tattoo artist can select and activate a tattoo machine to be used from a set of available tattoo machines, the selected tattoo machine being associated with the activating power supply, without touching any user interface of the tattoo machine controller unit shared between the available tattoo machines. This makes it easier to maintain the tattoo machine controller unit clean and sterile. By way of example, the tattoo machine power supply may be a tattoo machine battery pack. The battery pack may be mounted onto a tattoo machine.

According to an embodiment, wirelessly transmitting the activation signal comprises wirelessly transmitting the activation signal to a remote tattoo machine controller unit. Thereby, the tattoo machine controller unit may keep track of which tattoo machine power supply is currently active, for the purpose of e.g. updating settings of and sending commands to the currently active tattoo machine power supply.

According to an embodiment, the detection of a user interaction with the tattoo machine power supply comprises detecting the motion of a motion sensor, such as an accelerometer. Thereby, the tattoo artist does not need to touch any electronic user interface of the tattoo machine power supply either. This makes it easier to maintain also the tattoo machine clean and sterile. Furthermore, it facilitates protecting the entire power supply in a disposable plastic bag without impeding user interaction with the power supply. When the power supply is mounted on a tattoo machine, the tattoo machine may be automatically activated together with the power supply when lifted from e.g. a table.

According to an embodiment, the method comprises accessing configuration information stored in a memory; and configuring the tattoo machine power supply using said configuration information. The configuration information may be stored locally in the tattoo machine power supply, and/or received from the tattoo machine controller unit. By way of example, the configuration information may comprise a voltage setting determining the supply voltage to be provided to the tattoo machine. Automatically configuring the power supply when activating it even further reduces the need for interacting with a user interface during tattooing.

According to an embodiment, the method comprises synchronizing configuration information between the tattoo machine power supply and the tattoo machine controller unit. Thereby, any user interface of the remote tattoo machine controller unit will be synchronized with the settings of the currently active tattoo machine power supply, such that any relative setting changes, e.g. stepping up or down a voltage setting using a keypad, will depart from the individual setting of the activating power supply. Depending on the location of the stored configuration information, the configuration information may be wirelessly received from or transmitted to the tattoo machine controller unit.

According to an embodiment, the tattoo machine power supply is set in the active state based on a wirelessly received activation response. This adds an additional level of reliability to the system, and may be used for positively preventing that two power supplies are in active state simultaneously. By way of example, the response may be transmitted by a remote tattoo machine controller unit in conjunction with the de-activation of a previously active tattoo machine power supply.

According to an embodiment, the method comprises receiving a foot pedal command from the tattoo machine controller unit.

According to another aspect, the above mentioned problems are solved, or at least mitigated, by a method of operating a tattoo machine controller unit, the method comprising maintaining a list of devices recognized by the tattoo machine controller unit; wirelessly receiving an activation signal from an activating tattoo machine power supply; and updating the list of devices to indicate that the activating tattoo machine power supply is the currently active tattoo machine power supply to be controlled by the tattoo machine controller unit. Thereby, the controller unit may send control commands to the correct, i.e. currently active, power supply without the need for an operator to physically interact with the controller unit. The activating tattoo machine power supply may use its own identity to identify itself vis-a-vis the tattoo machine controller unit. The tattoo machine power supply may also, or as an alternative, identify the tattoo machine to which it is connected, and transmit the tattoo machine identity to the tattoo machine controller unit.

According to an embodiment, the method comprises synchronizing configuration information between the tattoo machine power supply and the tattoo machine controller unit. Thereby, any user interface of the remote tattoo machine controller unit will be synchronized with the actual settings of the currently active tattoo machine power supply. Depending on the location of the stored configuration information, the configuration information may be wirelessly received from or transmitted to the tattoo machine controller unit.

According to an embodiment, the method comprises receiving a signal from a foot pedal; and based on the received signal, wirelessly transmitting a command to the currently active tattoo machine power supply. Thereby, the foot pedal need not communicate with each individual power supply. Instead, the controller unit will automatically route any foot pedal commands to the currently active power supply only. The foot pedal may be connected to the tattoo machine controller unit in a wireless or wired manner.

According to an embodiment, the method comprises wirelessly transmitting an activation response to the activating tattoo machine power supply. This adds an additional level of reliability to the system.

According to an embodiment, the method comprises wirelessly transmitting a de-activation signal to a tattoo machine power supply other than the activating tattoo machine power supply. This adds an additional level of reliability to the system. The de-activation signal may be transmitted to all recognized power supplies, or to the most recently active power supply only.

According to an embodiment, the method comprises detecting when a battery pack is connected to battery charge terminals of the tattoo machine controller unit; determining a battery pack identity associated with the battery pack; and adding the battery pack to the list of devices recognized by the tattoo machine controller unit. The battery pack identity may be read from the battery pack or assigned to the battery pack by the tattoo machine controller unit.

According to yet another aspect, the above mentioned problems are solved, or at least mitigated, by a tattoo machine power supply comprising means for detecting a user interaction with the tattoo machine power supply for setting the tattoo machine power supply in an active state; electronics configured to, based on said user interaction, generate an activation signal; a wireless transmitter for transmitting the activation signal; and a wireless receiver for receiving, when the tattoo machine power supply is in the active state, remote control commands. The tattoo machine power supply may be configured to perform the method of controlling a tattoo machine power supply according to any of the embodiments described hereinbefore.

According to an embodiment, the wireless transmitter is configured to transmit the activation signal to a remote tattoo machine controller unit.

According to an embodiment, said means for detecting a user interaction with the tattoo machine power supply comprises a motion sensor, such as an accelerometer or the like, for sensing a motion of the power supply.

According to an embodiment, the tattoo machine power supply further comprises a first battery for supplying power to the tattoo machine. Preferably, the battery is rechargable.

According to an embodiment, the tattoo machine power supply is configured as an exchangeable battery pack adapted for being releasibly attached to a tattoo machine.

According to an embodiment, the tattoo machine power supply further comprises a second battery for supplying power to the tattoo machine, wherein the first and second batteries are arranged on either side of a recess for receiving a tattoo machine drive motor. Such a power supply may be attached to a tattoo machine without considerably changing the tattoo machine's overall shape or moving its center of gravity. In this way, the user experience/handling of a tattoo machine may be essentially the same regardless of whether it is powered by the battery pack or by a cable.

According to still another aspect, the above mentioned problems are solved, or at least mitigated, by a tattoo machine controller unit comprising a memory configured to maintain a list of devices recognized by the tattoo machine controller unit; a wireless receiver for receiving an activation signal from an activating tattoo machine power supply; and electronics configured to, based on a received activation signal from an activating tattoo machine power supply, update the list of recognized devices to indicate that the activating tattoo machine power supply is the currently active tattoo machine power supply to be controlled by the tattoo machine controller unit. The tattoo machine controller unit may be configured to perform the method of operating a tattoo machine controller unit according to any of the embodiments described hereinbefore.

According to an embodiment, the tattoo machine controller unit further comprises a battery pack charging station; and a user inter face panel, which is attached to and held clear of the battery pack charging station by a support post, which extends downwards from the user interface panel so as to allow a plastic bag to be slipped over the user interface panel from above. Thereby, the user interface panel may be protected from contamination by a plastic bag, while the battery pack charging station may still be maintained outside the bag for e.g. allowing access to the battery charge terminals and/or ventilating the charging station electronics. The bag's opening will face downwards, such that the weight of the bag will maintain the bag in place, and such that the user interface panel will be completely protected from any dripping.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, where the same reference numerals will be used for similar elements, wherein.

DETAILED DESCRIPTION OF THE EXEMPLARY EMBODIMENTS

Figure 1:
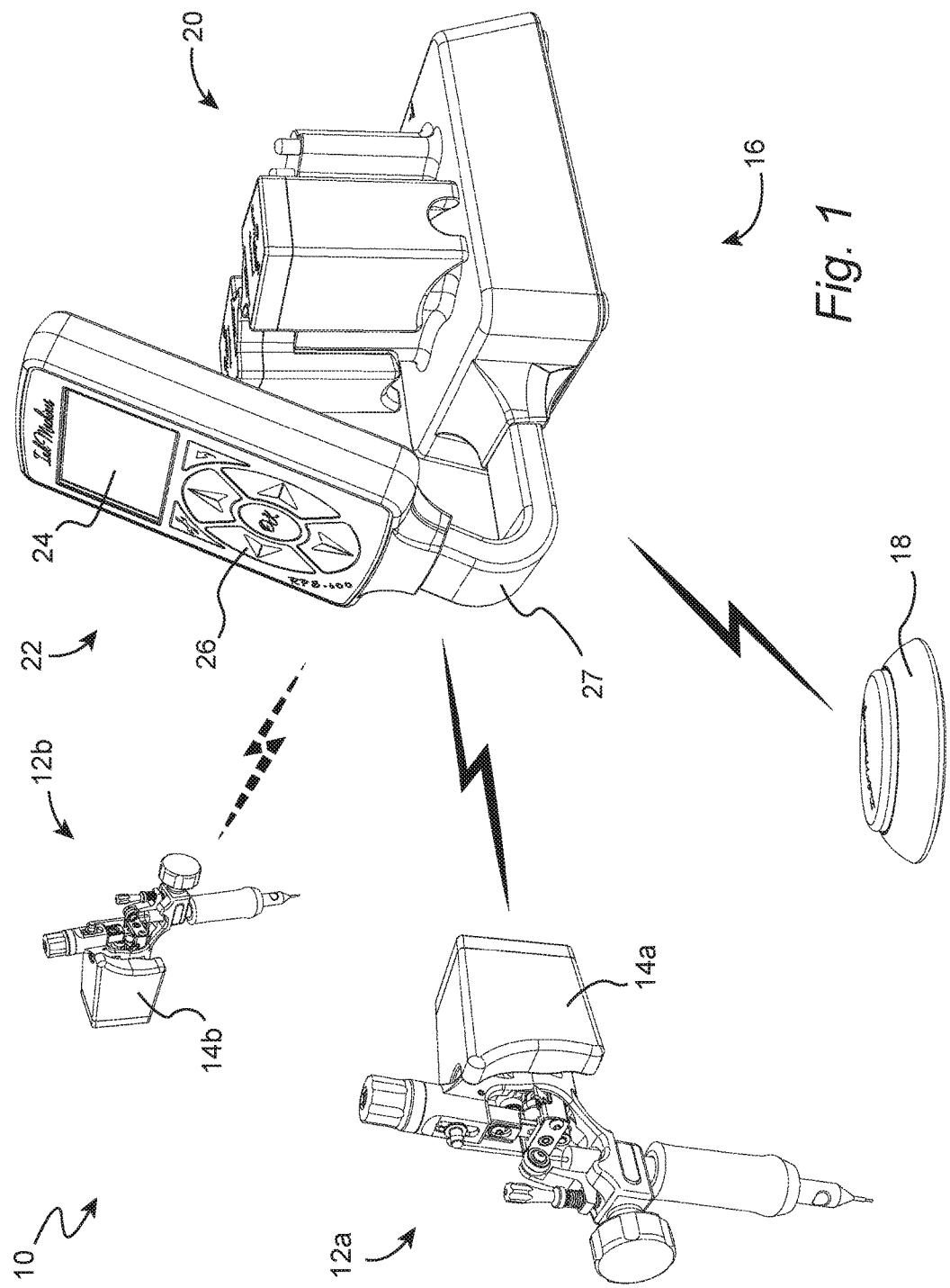
FIG. 1 is a diagrammatic view in perspective of a tattoo system.

FIG. 1 illustrates an exemplary tattoo system 10, which comprises a first hand-held tattoo machine 12a and a second hand-held tattoo machine 12b. The first tattoo machine 12a is provided with a first tattoo machine power supply 14a, and the second tattoo machine 12b is provided with a second tattoo machine power supply 14b. Each of the two power supplies 14a-b is configured as a battery pack, which is attached to the respective tattoo machine 12a-b. The first power supply 14a is electrically connected to the first tattoo machine 12a for providing the first tattoo machine 12a with electrical power, whereas the second power supply 14b is electrically connected to the second tattoo machine 12b for providing the second tattoo machine 12b with electrical power. The system 10 further comprises a tattoo machine controller unit 16, which may be used for controlling either of the two tattoo machines 12a-b by transmitting control commands to the respective power supplies 14a-b. The controller unit 16 also communicates with a foot pedal 18, which allows a tattoo machine operator to transmit foot pedal commands, e.g. for starting or stopping the tattoo machines 12a-b, to the controller unit 16.

The controller unit 16 comprises a battery pack charging station 20, which allows charging battery packs to be connected to tattoo machines, and a user interface panel 22, which allows an operator to modify and review settings of the controller unit 16 and/or power supplies 14. The user interface panel 22 is provided with a display 24 and a keypad 26. In order to allow a plastic bag to be slipped over the user interface panel 22 from above, the panel 22 is attached to the battery pack charging station 20 by a support post 27, and held upright at a distance from the battery pack charging station 20.

Figure 2:
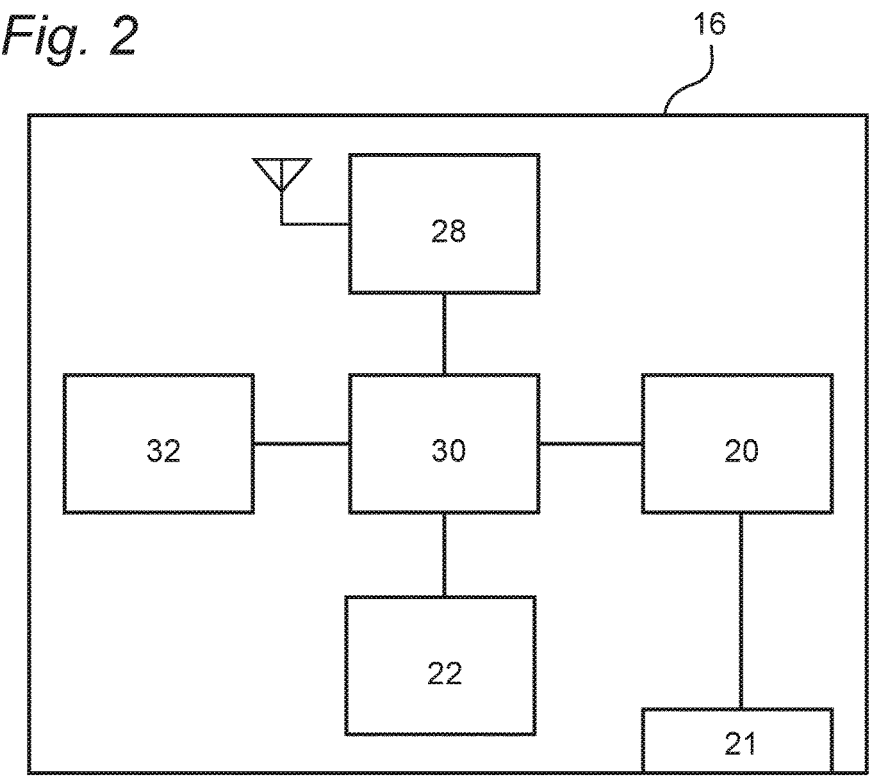
FIG. 2 is a schematic block diagram of a tattoo machine controller unit.

Turning now to FIG. 2, the controller unit 16 is provided with a wireless transceiver 28 for wirelessly communicating with each of the power supplies 14a-b and the foot pedal 18, e.g. by radio or infrared communication. In order to warrant operation also in the case where there is no clear line of sight between e.g. the power supplies 14a-b and the controller unit 16, it is preferred that the communication takes place over a radio interface. A short-range radio interface may be preferred in order to avoid interference with other wireless systems. In particular, ZigBee provides low latency and long battery life, and is therefore particularly well suited for communication between the controller unit 16 and the foot pedal 18 and power supplies 14a-b. The controller unit 16 also comprises a processor 30 and a memory 32. The processor 30 may be configured to process operator commands received from the foot pedal 18 and/or user interface panel 22; update the memory 32 with tattoo machine controller unit settings; generate control commands to be transmitted to power supplies 14a-b; and update the display 24 with control setting information. The processor may also control the battery pack charging station 20, and receive information from the battery pack charging station 20 as well as from any power supply connected to the charging station 20 via a docking interface 21.

Even though the controller unit 16 may communicate with any or all of the power supplies 14a-b, it is configured to allow the operator to control only one of the power supplies 14a-b at a time. The power supply to be controlled by the operator is called the currently active power supply. In the exemplary system overview of FIG. 1, the first power supply 14a is the currently active power supply, to which the controller unit 16 is configured to transmit control commands received via the user interface panel 22 or from the foot pedal 18. The second power supply 14b is, in FIG. 1, in a dormant state. For the purpose of routing control commands to the correct power supply 14a-b, the memory 32 is configured to maintain a list of devices recognized by the tattoo machine controller unit 16. The processor 30 is configured to maintain the list updated with information indicating which of the power supplies 14a-b is the currently active tattoo machine power supply to be controlled by the tattoo machine controller unit 16. When the controller unit 16 receives an operator command from e.g. the foot pedal, the processor 30 accesses the memory 32 and identifies which of the power supplies 14a-b is the currently active power supply, and then automatically routes the foot pedal command to the currently active power supply 14a via the wireless transceiver interface 28. The processor 30 may also generate control messages based on input from the user interface panel 22 and transmit to the currently active power supply 14a. Such control messages may comprise voltage and/or current settings for the electrical power to be supplied by the currently active power supply 14a to the tattoo machine 12a, and/or rpm settings for the reciprocating motion of the tattoo needle. The processor 30 may also update status information on the display 26 (FIG. 1) based on input from the foot pedal 18, the key pad 24, the battery pack charging station 20, and/or any of the power supplies 14a-b recognized by the controller unit 16.

An operator may trigger a dormant power supply 14b to wirelessly transmit an activation signal to the controller unit 16. When the activation signal has been received by the controller unit 16, the processor 30 updates the list of recognized devices in the memory 32 to indicate that the activating tattoo machine power supply 14b, i.e. the source of the activation signal, is the currently active tattoo machine power supply to be controlled by the tattoo machine controller unit 16. Thereafter, the first power supply 14a will no longer be the currently active power supply and may enter the dormant state. The de-activating power supply 14a may enter dormant state based on e.g. a time-out, during which no commands are received from the controller unit 16, or based on a de-activation signal transmitted from the controller unit 16 to the de-activating power supply 14a. The controller unit 16 may optionally confirm to the activating power supply 14b that it is now the currently active power supply by transmitting an activation response signal to the activating power supply 14b. The controller unit may also, optionally, transmit any configuration information stored in the memory 32 to the activating power supply 14b. Such configuration information may comprise voltage and/or current settings for the electrical power to be supplied by the activating power supply 14b to the tattoo machine 12b, and/or rpm settings.

Figure 3:
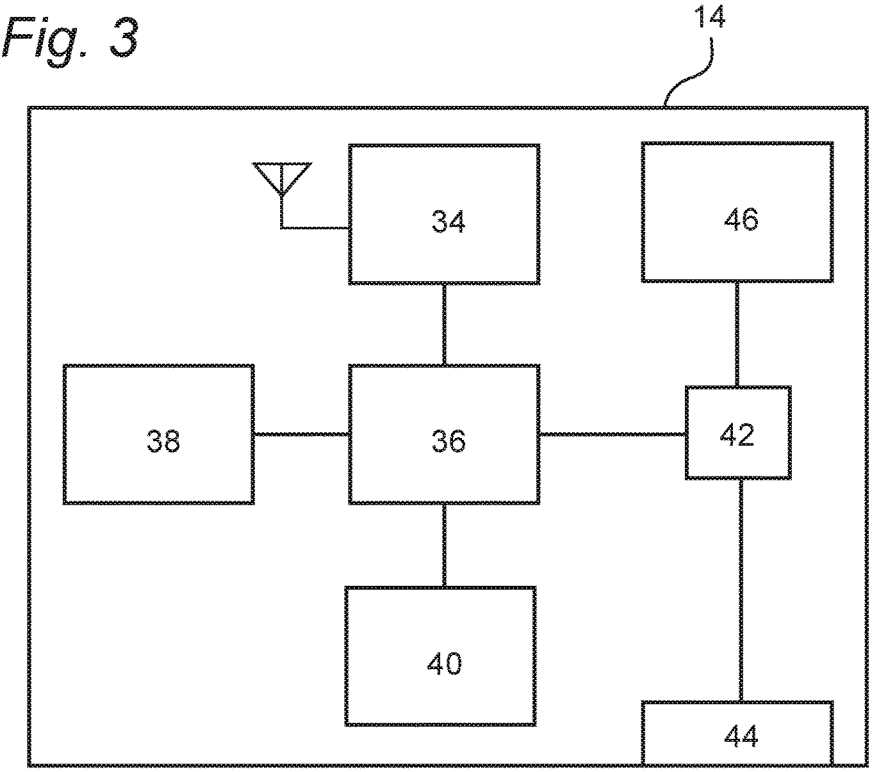
FIG. 3 is a schematic block diagram of a tattoo machine power supply.

FIG. 3 schematically illustrates functional blocks of a tattoo machine power supply 14, such as any of the previously illustrated power supplies 14a-b. The power supply 14 comprises a wireless transceiver 34 for communicating with the controller unit 16, a processor 36, a memory 38, a sensor 40 for detecting the interaction of an operator with the power supply 14, and a power controller 42 for controlling the provision of electrical power from a power source to a tattoo machine, such as any of the tattoo machines 12a-b, via an electrical interface 44. The power controller may, by way of example, be configured as a DC/DC converter unit controlled by the processor 36, or a transistor or switch for on/off regulation. As will be illustrated further below, the electrical interface 44 may be configured as a set of electrical contact terminals. The electrical power source may, by way of example, be a cable connected to an AC or DC voltage source or, as is illustrated in FIG. 3, one or several batteries 46. The sensor 40 may, by way of example, be any type of motion sensor, such as an accelerometer, for detecting when the operator moves the power supply 14. Thereby, the processor 36 may automatically detect when the operator lifts a tattoo machine provided with the power supply 14 from a table, and may automatically activate the power supply 14 and the associated tattoo machine.

The power supply 14 may initially be in a dormant state. When the sensor 40 detects a user interaction, the processor 36 generates an activation signal, which is wirelessly transmitted to the controller unit 16 via the transceiver 34. The power supply may then enter an active state, in which it is responsive to commands from the controller unit 16 and/or the foot pedal 18. The active state may be entered either directly, or in response to an activation response received from the controller unit 16. When the power supply is in active state, the processor 36 may, based on control signals received from the controller unit 16 or the foot pedal 18, trigger the power controller 42 to supply power from the power source 46 to the tattoo machine via the interface 44. Voltage, current and/or rpm settings governing the power provision may be obtained from the memory 38, and/or from the controller unit 16 via the wireless transceiver 34.

Figure 4A:
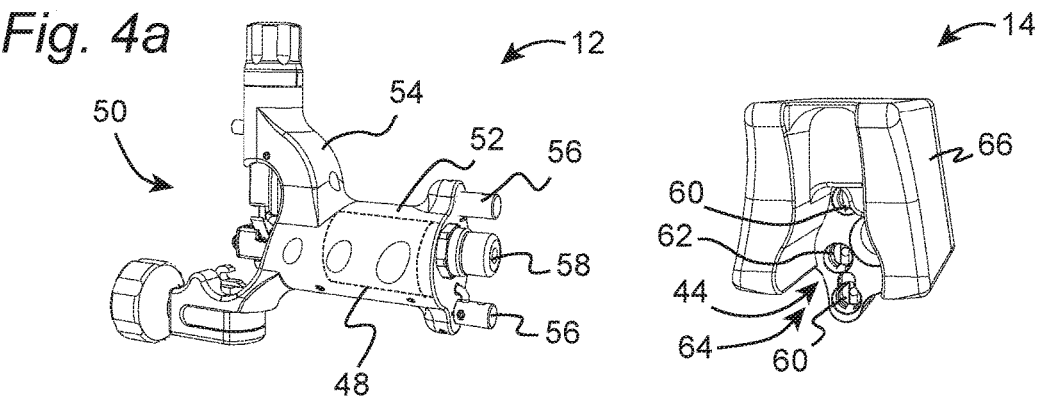
FIG. 4a is a diagrammatic view in perspective of a tattoo machine and a tattoo machine power supply prior to connecting.

FIG. 4a illustrates a tattoo machine 12 and a power supply of battery pack type 14. The tattoo machine 12 is electrically powered and of rotary type, i.e. driven by a rotary electric motor 48, the motion of which is converted to oscillatory tattoo needle motion via a transmission arrangement 50. The motor 48 is located in a motor housing portion 52 of a tattoo machine chassis 54. The motor 48 may be configured to operate on DC electrical power, which may be provided via a pair of terminals 56. An RCA connector 58 provides an auxiliary means of supplying power to the tattoo machine 12, e.g. via an RCA cable (not shown) from a controller unit 16.

The power supply 14 is provided with an electrical interface 44 having a pair of terminals 60 mating with the terminals 56 of the tattoo machine 12, and a third terminal 62 to be described further below. The terminals 60 are located in a recess 64 in the housing 66 of the power supply 14. The recess 64 is shaped to receive the motor housing 52, such that the power supply 14 may be slipped onto the motor housing 52 of the tattoo machine 12 in the manner illustrated by an arrow in FIG. 4b. When the power supply 14 is mounted on the tattoo machine 12, the terminals 60 of the power supply 14 are in electrical contact with the mating terminals 56 of the tattoo machine 12. As has been explained hereinbefore, the power supply 14 may have an identity for the purpose of identifying itself vis-a-vis the controller unit 16. According to an embodiment, the power supply 14 may read an identity of the tattoo machine 12 upon connection to the tattoo machine 12, and use that tattoo machine identity for identifying itself vis-a-vis the controller unit 16. Such a tattoo machine identity may be read by the power supply 14 by communicating with the tattoo machine 12 via the electrical interface 44, or by using an optional RFID tag reader provided in the power supply 14, which may read the identity of an RFID tag (not illustrated) attached to the tattoo machine 12. The tattoo machine identity may be stored in the memory 38 of the power supply 14, and communicated to the controller unit 16 by the wireless transceiver 34 when the power supply 14 is activated. Such an embodiment may have the advantage that any control settings, such as voltage and RPM, are associated with the tattoo machine 12 rather than with the tattoo machine power supply 14.

Figure 4B:
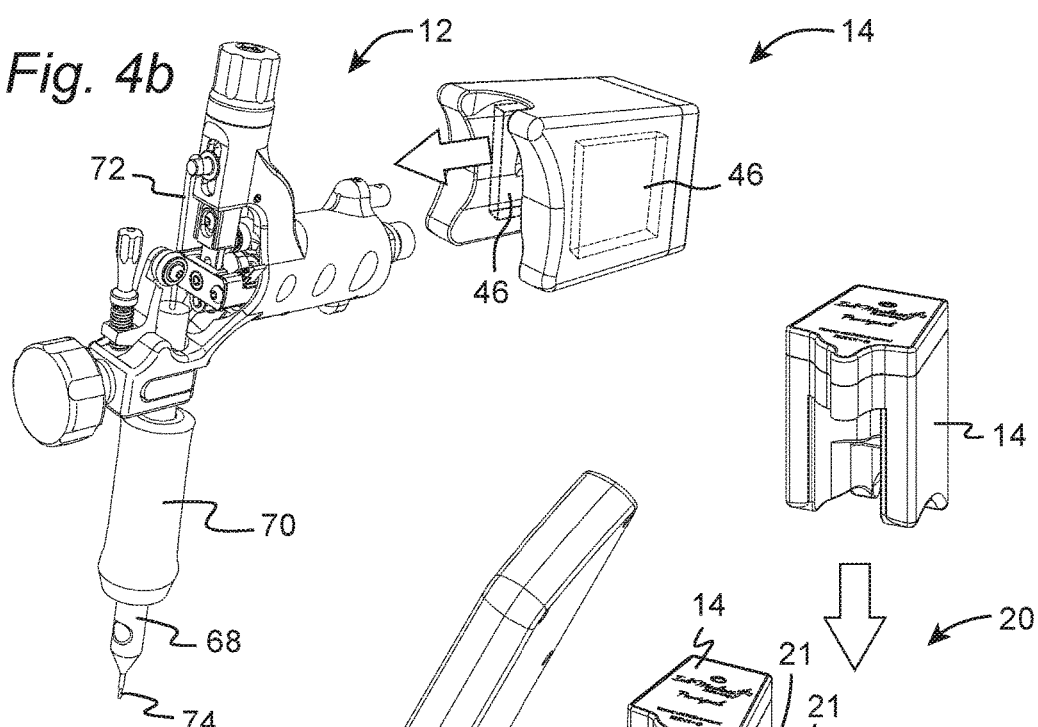
FIG. 4b is a diagrammatic view in perspective of the tattoo machine and tattoo machine power supply of FIG. 4a after connecting.

In the view of FIG. 4b, the tattoo machine 12 is illustrated provided with a tube 68 enclosed by a handgrip 70. The tattoo machine 12 is configured to vertically reciprocate a needlebar 72, which extends through the tube 68, such that the needlebar 72 is axially moved along the tube 68 in an oscillating manner. A lower end 74 of the needlebar 72 may be provided with one or several tattoo needles, which are to penetrate the skin tissue of a human or animal to be tattooed, and release thereinside the ink that will form the body artwork.

The power supply 14 is provided with a pair of batteries 46, which are located on opposite sides of the motor 48 when the power supply 14 is mounted onto the tattoo machine 12.

Figure 5:
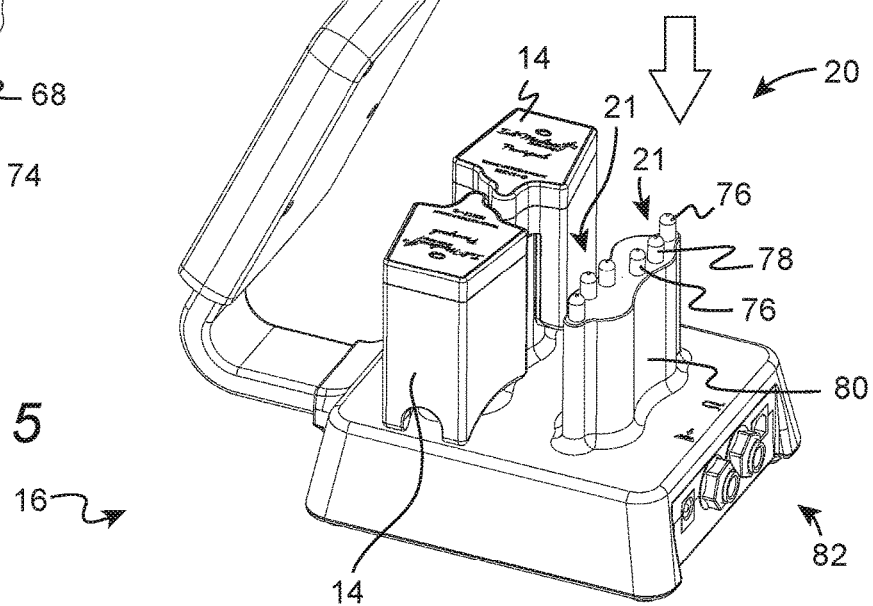
FIG. 5 is a diagrammatic view in perspective illustrating the docking of a tattoo machine power supply to a tattoo machine controller unit.

Turning now to FIG. 5, the power supply 14 may be docked with the battery pack charging station 20 of the controller unit 16. The battery pack charging station 20 has four docking interfaces 21 allowing simultaneous docking and charging of four power supplies. In the illustrated view, two of the docking interfaces are occupied, and hidden, by docked power supplies 14. Each docking interface 21 comprises a pair of charging terminals 76 for mating with the terminals 60 (FIG. 4a) of the power supply 14, for charging the batteries 46, and a third, communication terminal 78 for mating with the third terminal 62 of the power supply 14. The communication terminal 78 allows communication between the power supply 14 and the controller unit 16. The terminals 76, 78 are located on a protrusion 80 shaped so as to extend into the recess 64 of a power supply 14 when docked. A power supply 14 may be docked by lowering it over the protrusion 80 such that the terminals 60, 62 mate with the terminals 76, 78 respectively. When docking a power supply 14, the controller unit 16 identifies whether the power supply 14 is in the list of devices recognized by the controller unit. If not, the controller unit automatically adds an identity of the docked power supply 14 to the list. By way of example, each identity may be formed by one or several digits, characters, or binary codes uniquely representing the respective power supply 14. The identity may be received from or assigned to the power supply 14 via the communication terminal 78. Thereby, power supplies 14 may automatically be paired with the controller unit 16 by placing them in the charging station 20. The controller unit 16 may also automatically start charging the batteries 46 of a power supply 14 when placed in the charging station 20.

For maximum versatility, the controller unit may also be provided with connectors 82 for connecting legacy, wired tattoo machines and foot pedals.

The invention has mainly been described above with reference to a few embodiments. However, as is readily appreciated by a person skilled in the art, other embodiments than the ones disclosed above are equally possible within the scope of the invention, as defined by the appended patent claims.

For example, tattoo machines of rotary type have been described. The invention may also be used for other types of tattoo machines, such as coil machines. Moreover, the power supplies 14 disclosed in detail hereinbefore are configured to be releasibly attached to tattoo machines 12. As an alternative, the power supplies may be integrated with or attached to their respective tattoo machines in a fixed manner.

It has been described how an activation signal may be sent from an activating tattoo machine power supply 14b to a tattoo machine controller unit 16. However, it is not necessary that the activation signal be transmitted only to the tattoo machine controller unit 16. As a complement, or as an alternative, the activation signal may be transmitted from the activating power supply 14b directly to a currently active power supply 14a, which is to de-activate based on reception of said activation signal without the involvement of a tattoo machine controller unit 16. According to such an alternative embodiment, the controller unit 16 may address any control commands to all tattoo machine power supplies 14a-b of the system 10, and the power supplies 14a-b keep track among themselves which power supply is currently active, i.e. is to react to the control commands from the controller unit 16.

Hereinbefore, it has been described how a power supply 14b transmits an activation signal directly to a controller unit 16. Alternatively, the power supply 14b may transmit the activation signal to the controller unit 16 via another device, such as via another power supply 14a or via a foot pedal 18. Such alternatives are also intended to be covered by the appended claims.

Several of the technical solutions disclosed herein may also be used independently of the claimed invention. Such technical solutions may form the basis of divisional applications to be filed. By way of example, according to a second inventive concept, there is provided a tattoo machine battery pack comprising a first and a second battery for supplying power to a tattoo machine, wherein the first and second batteries are arranged on either side of a recess for receiving a tattoo machine drive motor. Such a power supply may be attached to a tattoo machine without considerably changing the tattoo machine's shape or moving its center of gravity. In this way, the user experience/handling of a tattoo machine may be essentially the same regardless of whether it is powered by a battery pack or connected by a cable to a legacy (wired) tattoo machine controller unit.

According to a third inventive concept, there is provided a tattoo machine controller unit comprising a battery pack charging station; and a user inter face panel, which is attached to and held clear of the battery pack charging station by a support post, which extends downwards from the user interface panel so as to allow a plastic bag to be slipped over the user interface panel from above. Thereby, the user interface panel may be protected from contamination by a plastic bag, while the battery pack charging station may still be maintained outside the bag for e.g. allowing access to the docking interface(s) and/or ventilating the charging station electronics. The bag's opening will face downwards, such that the weight of the bag will maintain the bag in place, and such that the user interface panel will be completely protected from any dripping.

According to a fourth inventive concept, there is provided a tattoo machine power supply comprising electronics for reading an identity of a tattoo machine; electronics configured to generate an identification signal based on the read identity; and a wireless transmitter configured to transmit the identification signal to a tattoo machine controller unit.

The invention claimed is:

1. A tattoo machine power supply comprising:
   means for detecting a user interaction with the tattoo machine power supply for setting the tattoo machine power supply in an active state;
   electronics configured to, based on said user interaction, generate an activation signal;
   a wireless transmitter for transmitting the activation signal; and
   a wireless receiver for receiving remote control commands when the tattoo machine power supply is in the active state.

2. The tattoo machine power supply according to claim 1, wherein the wireless transmitter is configured to transmit the activation signal to a remote tattoo machine controller unit.

3. The tattoo machine power supply according to claim 1, wherein said means for detecting a user interaction with the tattoo machine power supply comprises a motion sensor configured to sense a motion of the power supply.

4. The tattoo machine power supply according to claim 1, further comprising a first battery configured to supply power to the tattoo machine.

5. The tattoo machine power supply according to claim 4, the tattoo machine power supply being configured as an exchangeable battery pack adapted for being releasibly attached to a tattoo machine.

6. The tattoo machine power supply according to claim 1, further comprising a second battery for supplying power to the tattoo machine, wherein the first and second batteries are arranged on either side of a recess configured to receive a tattoo machine drive motor.

7. A tattoo machine power supply comprising:
   a sensor configured to detect a user interaction with the tattoo machine power supply for setting the tattoo machine power supply in an active state;
   a processor configured to, based on said user interaction, generate an activation signal;
   a wireless transmitter for transmitting the activation signal; and
   a wireless receiver for receiving remote control commands when the tattoo machine power supply is in the active state.

8. The tattoo machine power supply according to claim 7, wherein the wireless transmitter is configured to transmit the activation signal to a remote tattoo machine controller unit.

9. The tattoo machine power supply according to claim 7, wherein said sensor comprises a motion sensor configured to sense a motion of the power supply.

10. The tattoo machine power supply according to claim 7, further comprising a first battery configured to supply power to the tattoo machine.

11. The tattoo machine power supply according to claim 10, the tattoo machine power supply being configured as an exchangeable battery pack adapted for being releasibly attached to a tattoo machine.

12. The tattoo machine power supply according to claim 7, further comprising a second battery for supplying power to the tattoo machine, wherein the first and second batteries are arranged on either side of a recess configured to receive a tattoo machine drive motor.

* * * * *